US008690863B2

(12) United States Patent
Chan et al.

(10) Patent No.: US 8,690,863 B2
(45) Date of Patent: Apr. 8, 2014

(54) LASER-INDUCED TRANSEPIDERMAL ELIMINATION OF CONTENT BY FRACTIONAL PHOTOTHERMOLYSIS

(75) Inventors: Kin F. Chan, San Jose, CA (US); Basil M. Hantash, East Palo Alto, CA (US); G. Scott Herron, La Honda, CA (US); Vikramaditya P. Bedi, Redwood City, CA (US)

(73) Assignee: Reliant Technologies, LLC, Hayward, CA (US)

( * ) Notice: Subject to any disclaimer, the term of this patent is extended or adjusted under 35 U.S.C. 154(b) by 2311 days.

(21) Appl. No.: 11/548,248

(22) Filed: Oct. 10, 2006

(65) Prior Publication Data

US 2007/0198068 A1    Aug. 23, 2007

Related U.S. Application Data

(60) Provisional application No. 60/725,198, filed on Oct. 10, 2005.

(51) Int. Cl.
   *A61B 18/20*    (2006.01)
(52) U.S. Cl.
   USPC .................................. 606/9; 606/2; 128/898
(58) Field of Classification Search
   USPC ...................... 128/898; 606/2–19; 607/88–95
   See application file for complete search history.

(56) References Cited

U.S. PATENT DOCUMENTS

| 5,290,272 | A | 3/1994 | Burstein et al. |
|---|---|---|---|
| 5,290,273 | A | 3/1994 | Tan |
| 5,339,347 | A | 8/1994 | Slatkin et al. |
| 5,360,447 | A | 11/1994 | Koop |
| 5,643,252 | A | 7/1997 | Waner et al. |
| 6,027,496 | A | 2/2000 | Loomis et al. |
| 6,059,820 | A | 5/2000 | Baronov |
| 6,074,382 | A | 6/2000 | Asah et al. |
| 6,219,575 | B1 | 4/2001 | Nemati |
| 6,315,772 | B1 | 11/2001 | Marchitto et al. |
| 6,632,219 | B1 | 10/2003 | Baranov et al. |
| 6,997,923 | B2 | 2/2006 | Anderson et al. |
| 2002/0161357 | A1 | 10/2002 | Anderson et al. |
| 2003/0032950 | A1 | 2/2003 | Altshuler et al. |
| 2003/0055413 | A1 | 3/2003 | Altshuler et al. |
| 2003/0216719 | A1 | 11/2003 | DeBenedictis et al. |
| 2004/0002704 | A1 | 1/2004 | Knowlton et al. |
| 2004/0225339 | A1 | 11/2004 | Yaroslavsky et al. |

(Continued)

FOREIGN PATENT DOCUMENTS

WO    WO 2004/037068 A2    5/2004
WO    WO 2004/086947 A2    10/2004

(Continued)

OTHER PUBLICATIONS

Gerhard Schwinger et al, *Structural and mechanical aspects of the skin of Bufo marinus (Anura, Amphibia)*, Tissue & Cell, 2001, pp. 541-547, vol. 33.

(Continued)

*Primary Examiner* — Aaron Roane
(74) *Attorney, Agent, or Firm* — Wood, Herron & Evans LLP

(57) ABSTRACT

Subjects treated with nonablative fractional photothermolysis (FP) have an intact stratum corneum, but can have microscopic lesions and vacuole formation within the epidermis. The vacuoles thus formed can trap dermal material and extrude it through the epidermis. Thus, FP can be used for the treatment of recalcitrant melasma, solar elastosis, and tattoos.

39 Claims, 3 Drawing Sheets

(56) References Cited

U.S. PATENT DOCUMENTS

| | | | |
|---|---|---|---|
| 2005/0049582 A1 | 3/2005 | DeBenedictis et al. |
| 2005/0222555 A1 | 10/2005 | Manstein et al. |
| 2005/0285928 A1 | 12/2005 | Broome et al. |
| 2006/0004306 A1 | 1/2006 | Altshuler et al. |
| 2006/0004347 A1 | 1/2006 | Altshuler et al. |
| 2006/0007965 A1 | 1/2006 | Tankovich et al. |
| 2006/0020309 A1 | 1/2006 | Altshuler et al. |
| 2006/0058712 A1 | 3/2006 | Altshuler et al. |

FOREIGN PATENT DOCUMENTS

| | | | |
|---|---|---|---|
| WO | WO 2005/096981 | A2 | 10/2005 |
| WO | WO 2005/099369 | A2 | 10/2005 |
| WO | WO 2005/102153 | A1 | 11/2005 |
| WO | WO 2005/107848 | A2 | 11/2005 |

OTHER PUBLICATIONS

Thomas Y. Woo et al, *Disorders of Transepidermal Elimination—Part 2*, International Journal of Dermatology, Jul.-Aug. 1985, pp. 337-348, vol. 24.

Fujii, H. et al., "Multispot Laser Photocoagulation System Using a Fiber Bundle Scanner", Applied Optics, Oct. 1, 1982, pp. 3437-3442, vol. 21, No. 19.

Manstein, D. et al., "Fractional Photothermolysis: A New Concept for Cutaneous Remodeling Using Microscopic Patterns of Thermal Injury," Lasers in Surgery and Medicine, 2004, pp. 426-438, vol. 34.

U.S. Appl. No. 60/458,770, filed Mar. 27, 2003, 36 pages.

Anderson et al, U.S. Appl. No. 60/258,855, filed Dec. 28, 2000, pp. 1-3, 5, 6, 8-15 and Figures 22A and 22B.

PCT International Search Report and Written Opinion, PCT/US06/39829, Jul. 11, 2007, 8 pages.

LASER-INDUCED TRANSEPIDERMAL ELIMINATION OF CONTENT BY FRACTIONAL PHOTOTHERMOLYSIS

CROSS-REFERENCE TO RELATED APPLICATION

This application claims the benefit of U.S. Provisional Patent Application Ser. No. 60/725,198, by Kin F. Chan and Basil M. Hantash, filed on Oct. 10, 2005, the disclosure of which is incorporated herein by reference in their entirety.

FIELD OF THE INVENTION

This invention relates generally to irradiating tissue with electromagnetic radiation. More particularly, it relates to cosmetic methods of using electromagnetic radiation to transport and eliminate dermal content through the skin.

BACKGROUND OF THE INVENTION

The skin is a complex metabolic organ with unique structure and function (M. W. Greaves, "Physiology of Skin," *J. Invest. Dermatol.* 67(1), 66-69 (1976)). It is composed of three primary layers, namely the epidermis, dermis, and subcutaneous. The epidermis comprises the upper or outer layers of the skin, is nonvascular, and varies in thickness over different parts of the body. The epidermis itself is composed of several different layers, specifically the stratum corneum, stratum lucidum, stratum granulosum stratum spinosum, and stratum basale layers.

The uppermost or outermost layer of the skin is the stratum corneum, also known as the "horny layer" of the skin, is composed mainly of dead cells that lack nuclei, the uppermost of which slough off over time. The cells within the stratum corneum are flat and scale-like in shape. These cells, composed mainly of the protein keratin, are arranged in overlapping layers, imparting a tough and hydrophobic nature to the stratum corneum.

Below the stratum corneum is the stratum lucidum, a homogeneous translucent band, much thinner than the layers above and below it. Below the stratum lucidum layer of the epidermis is the stratum granulosum, composed of two or three rows of flat cells composed mainly of keratohyalin, which is transformed into keratin in more superficial layers. Stratum spinosum lies below the stratum granulosum and is composed of several layers of polygonal cells known as "prickle cells." The number of layers of cells in the stratum granulosum varies over different regions of the body.

Below the stratum spinosum layer is the stratum basale layer, also known as the stratum germinativum, the deepest layer of the epidermis. The stratum basale is composed of columnar cells which are continually dividing to produce new skin cells. It is the cells in the stratum basale that produce melanin. Over time, the cells produced in the stratum basale move upward and away from the blood supply, and their cell contents and shapes change, forming the different layers of the epidermis. Under normal conditions, the basal layer cells migrate upward over the course of two weeks to create the stratum spinosum and stratum granulosum. An additional two weeks elapses before those cells are exfoliated from the stratum corneum, the non-viable selectively permeable barrier component of skin. Thus, exfoliation is a constitutive function of healthy normal skin.

The dermis is the inner layer of the skin containing blood capillaries, blood vessels, lymph vessels, hair follicles, and various glands. The dermis is composed of felted connective tissue containing elastin, collagen and fat. The dermis is divided into the upper, papillary layer and the lower, reticular layer.

The papillary layer of the dermis contains a large number of papillae, which rise perpendicularly from its surface. The papillary layer of the dermis also contains blood capillaries which carry nutrients to and remove waste from the dividing cells in the stratum basale.

The reticular layer of the dermis contains the blood vessels, sebaceous glands, arrector pili muscles, sensory nerve fibers, hair follicles, hair roots, pacinian corpuscles, hair root plexus, and eccrine sweat glands.

At the base of the dermis lies the subcutis, also known as the hypodermis or superficial fascia, composed primarily of adipose tissue.

In addition to exfoliation of dead epidermal cells, the skin is also capable of removing dermal content through a viable epidermis. This process, known as transepidermal elimination, allows the disposal of foreign material aberrantly implanted in skin (T. Y. Woo and J. E. Rasmussen, "Disorders of transepidermal elimination. Part 2," *Int. J. Dermatol.* 24(6), 337-348 (1985)). Aberrant functioning of the transportation system can lead to several pathological skin conditions, such as Kyrle's disease, elastosis perforans serpiginosa, reactive perforating collagenosis, acquired perforating dermatosis, chondrodermatitis nodularis helices, and perforating folliculitis. These diseases share in common the physiological function of transepidermal elimination, albeit triggered by a stimulus that leads to a pathological state.

Electromagnetic radiation, particularly as produced by lasers, has been applied directly to the skin for treatment of dermatological conditions, for skin resurfacing, to reduce or eliminate rhytides, and to combat the effects of aging in the skin. Beyond treatment of the skin, electromagnetic radiation therapy has been used to increase the rate of wound healing, to reduce pain, to treat inflammatory conditions, as well as to reduce residual neurological deficits following stroke. When used for skin resurfacing, the effect of electromagnetic radiation on skin is primarily to heat the skin, producing thermal coagulation, cell necrosis, melting, welding and ablation, among other effects. Treatment with electromagnetic radiation can generally be divided into ablative and nonablative treatments. Ablation of the stratum corneum with electromagnetic radiation has been used for skin resurfacing and to perforate the skin to allow delivery of active substances and for the removal or monitoring of biological fluids or gasses. The use of nonablative electromagnetic irradiation of the skin has also been suggested to increase skin permeability by altering the lipids, water, and protein molecules present in the stratum corneum, by producing heat, and by producing pressure waves. However, nonablative electromagnetic radiation therapy has not been used for the treatment of unwanted skin conditions such as the presence of pigment in the dermis, a problem commonly seen by dermatologists treating melasma, tattoos, and post-inflammatory hyperpigmentation.

SUMMARY OF THE INVENTION

The present invention provides methods and apparatus for the transport and extrusion of dermal content through the skin. The methods include irradiating the skin with electromagnetic irradiation, particularly fractional photothermolysis, to create microscopic lesions that allow for dermal content to be exfoliated through the stratum corneum.

It has been found that using nonablative electromagnetic irradiation under particular fractional treatment parameters produce conditions in the skin that are highly favorable for increasing the rate at which undesirable dermal content is removed from the skin, while producing less damage to the skin and fewer side effects.

The nonablative fractional electromagnetic irradiation described herein penetrate deeper and with greater accuracy into the epidermal and dermal layers of the skin than have previous treatments, and produce unique effects within the epidermal and dermal layers of the skin, while producing fewer side effects in the region of skin that has been treated as compared with other electromagnetic irradiation.

The invention provides methods and apparatus for eliminating dermal content through the skin by exposing a region of the skin to fractional electromagnetic radiation to create treatment zones wherein the treatment zones have substantially intact stratum corneum and vacuoles below the stratum corneum, and encompassing the dermal content in the vacuoles wherein the dermal content is exfoliated through the skin. The electromagnetic radiation can be laser radiation, such as that obtained by the use of Fraxel® SR1500 laser system (Reliant Technologies, Inc., Mountain View, Calif.), with a wavelength between about 1200 nm to about 2000 nm, a pulse energy of about 1 mJ to about 50 mJ, and a spot size of about 10 µm to about 400 µm. The treatment zone can have a width of about 1 µm to about 1000 µm. The vacuole is present in the dermal layer of the treated region of the skin, and can have a depth of about 1 µm to about 1000 µm, or a depth of at least about 200 µm. The methods and apparatus of the invention can be used for eliminating dermal content such as recalcitrant melasma, Hori's macule, tattoo, post-inflammatory hyperpigmentation, melanin, solar elastosis, mucinosis, amyloidosis, or scar tissue.

BRIEF DESCRIPTION OF THE DRAWINGS

The invention has other advantages and features which will be more readily apparent from the following detailed description of the invention and the appended claims, when taken in conjunction with the accompanying drawings, in which:

FIG. 1A illustrates the paraffin embedded section showing the dermal lesion representing collagen coagulation; FIG. 1B illustrates the dermal collagen stained blue by Masson trichrome; FIG. 1C illustrates the nonstaining of the vacuolar content by Nitro Blue Tetrazolium Chloride; FIG. 1D illustrates the darkly stained melanin by Fontanan Masson where the melanin is present in the vacuole.

FIG. 2A shows DAB stained tissues where the elastin is clearly identified just beneath the DE junction in the dermis; FIG. 2B illustrates the DAB stained tissue where the elastin is absent throughout the epidermis except within the vacuoles; FIG. 2C illustrates the staining of the tissue samples with Vector® Novared; FIG. 2D illustrates the higher magnification of the staining of the tissue samples with Vector® Novared.

FIG. 3A illustrates the specimen using a laser with a wavelength of about 1550 nm, at 6 mJ and 60 µm spot size; FIG. 3B illustrates the specimen using a laser with a wavelength of about 1550 nm, at 10 mJ and 60 µm spot size; FIG. 3C illustrates the specimen using a laser with a wavelength of about 1550 nm, at 6 mJ and 140 µm spot size; FIG. 3D illustrates the specimen using a laser with a wavelength of about 1550 nm, at 10 mJ and 140 µm spot size.

DETAILED DESCRIPTION OF THE PREFERRED EMBODIMENTS

Figure 1:
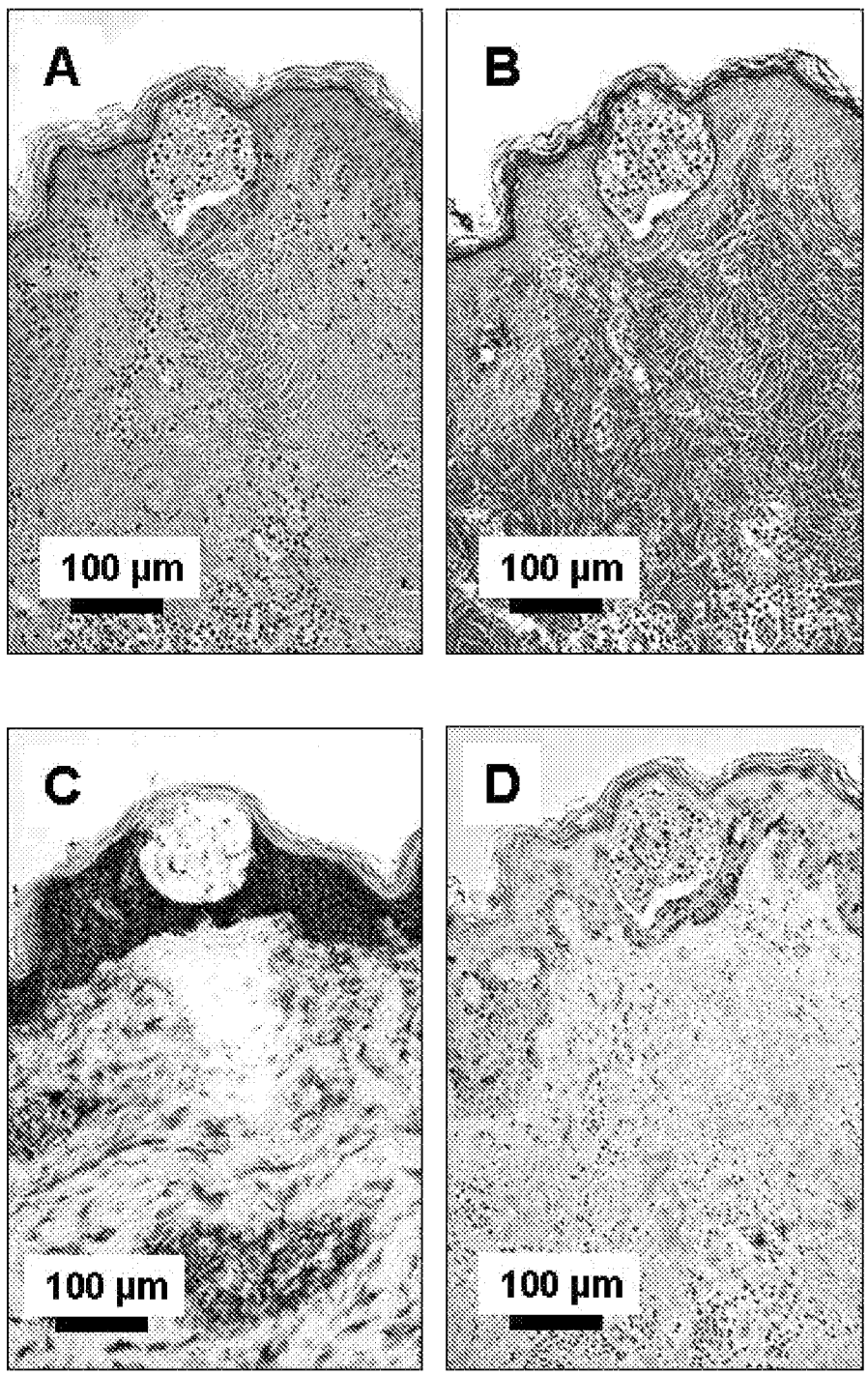
FIG. 1 illustrates the histological sections obtained from abdominal skin 1 day after fractional photothermolysis (FP) where the epidermal vacuoles overlies the thermal wound.

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. The practice of the present invention will employ, unless otherwise indicated, conventional methods of protein chemistry, biochemistry, recombinant DNA techniques and pharmacology, within the skill of the art. Such techniques are explained fully in the literature. See, e.g., Remington's Pharmaceutical Sciences, 19th Edition (Easton, Pa.: Mack Publishing Company, 1995); Carey and Sundberg Advanced Organic Chemistry $3^{rd}$ Ed. (Plenum Press) Vols A and B(1992).

The terms "treatment" and "therapy" include, but are not limited to, changes in the patient's status. The changes can be either subjective or objective and can relate to features such as symptoms or signs of the disease or condition being treated. For example, if the patient notes improvements in a dermatological condition, improvements in skin appearance, reduced discomfort or decreased pain, then successful treatment has occurred. Similarly, if the clinician notes objective changes, such as by histological analysis of a biopsy sample, then treatment has also been successful. Alternatively, the clinician may note a decrease in the size of lesions or other abnormalities upon examination of the patient. This would also represent an improvement or a successful treatment. Preventing the deterioration of a patient's status is also included by the term. Therapeutic benefit includes any of a number of subjective or objective factors indicating a response of the condition being treated, or an improvement in skin appearance, as discussed herein.

"Tissue" refers to an aggregate of cells that perform specific functions, and includes but is not limited to the skin, the adipose layer located below the skin, muscle, and organs. The cells of a tissue may or may not form a layer.

The term "viable" is used to describe tissue that is composed of living cells.

The term "discrete treatment zone" refers to a region of tissue within a larger volume of tissue which receives an effective amount of electromagnetic radiation. Thus, when treated with fractional electromagnetic radiation, the "treated region" will contain a plurality of "discrete treatment zones" to which an effective amount of electromagnetic radiation was directed, amid one or more regions to which electromagnetic radiation was not directed.

The term "physically intact stratum corneum" refers to a stratum corneum that may have been altered but that remains present following treatment.

The term "ablative" describes the removal of a significant amount of tissue from the site of treatment, substantially instantaneously.

The terms "nonablative" and "subablative" refer to processes that do not result in significant amounts of matter being removed from the site of treatment at the time of treatment.

"Vacuole" refers to a small cavity or space in a tissue, including but not limited to cavities or spaces that are filled with skin tissue, fluid, or gas. As used herein, a vacuole will be understood to have a minimum cross-sectional area of 900 $\mu m^2$ as measured in a plane roughly parallel to the skin surface.

For the purposes of this invention, the term "treatment zone width" is used to describe the distance measured on the treatment zone as twice the maximum of the distances in the plane of the skin that separates each treated point in the skin from the closest viable and undenatured region of the skin. In the case where a treatment zone is substantially circular, the cross-sectional width is equivalent to the diameter of the treatment zone.

The term "treatment zone density" refers to the number of discrete treatment zones present within the surface of the treated region of skin or tissue exposed to electromagnetic radiation.

For fractional treatments, "local fluence" refers to the energy density from an optical source impacting on the surface of a tissue measured to the $1/e^2$ intensity boundary of the beam. Thus, the local fluence is calculated based on the energy per spot size, and can be expressed in Joules per square centimeter ($J/cm^2$).

Recently, fractional electromagnetic irradiation of the skin have been found to produce fewer and less severe side effects than traditional bulk electromagnetic irradiation of the skin. Fractional electromagnetic irradiation involves generating a large number of discrete treatment zones within a larger treated region of tissue. In fractional treatment, the electromagnetic radiation impacts on only relatively small, discrete treatment zones, instead of impacting on the entire region of tissue undergoing treatment as in bulk treatment. Thus, when used on the skin, a significant portion of the surface area and of the volume of skin within the larger treatment region is spared the insult of electromagnetic radiation. As with traditional bulk treatments, the effects of the electromagnetic radiation on the discrete treatment zones of the tissue can include thermal coagulation, cell necrosis, melting, welding, ablation, and gross alteration and/or stimulation of the structure of the extra-cellular matrix and of the extra-cellular matrix materials. But following fractional treatments, only the portion of the tissue within the discrete treatment zones experience these effects. By controlling treatment parameters, specific treatment results such as the spacing of the discrete treatment zones within the treated region of tissue can be accurately controlled, the extent of tissue damage within the discrete treatment zones can be controlled (including the depth of effects into the epidermis and dermis), as well as the amount of viable tissue surrounding the discrete treatment zones can be controlled.

When electromagnetic radiation directly impacts on a portion of tissue, the tissue immediately adjacent to the site where the radiation impacted, under certain treatment parameters, can still receive enough conducted heat to thermally alter the surrounding tissue. Under fractional treatments, when significant heat is conducted from a discrete treatment zone into surrounding tissue to thermally alter the surrounding tissue, the discrete treatment zones will be surrounded by a relatively narrow "heat shock zone." The tissue in the heat shock zone has been heated to super-physiologic temperatures which produce thermal alteration, but a significant portion of the cells remain viable. The change from the discrete treatment zone into the heat shock zone and into the untreated zone, or from the discrete treatment zone into the untreated zone is gradual, not abrupt. Thus, fractional electromagnetic irradiation will produce discrete treatment zones surrounded by heat shock zones, which in turn are completely surrounded by a large volume of living tissue within the region of tissue that has undergone treatment.

Thus, fractional treatment methods make it possible to leave substantial volumes of tissue within the treatment region untreated by the electromagnetic radiation. When adequate amounts of viable tissue remain surrounding the discrete treatment zones following treatment, the viable tissue is able to assist in the rapid recovery of the discrete treatment zones, thus reducing the side effects of the electromagnetic irradiation within the region of tissue that was treated, and increasing the rate of recovery of the discrete treatment zones by stimulating skin remodeling and wound repair mechanisms.

On a microscopic level, skin that has been treated with nonablative fractional electromagnetic irradiation retains a physically intact stratum corneum while the tissue below the stratum corneum has been thermally altered. By maintaining a physically intact stratum corneum, the stratum corneum is still capable of providing protection from infection.

Using treatment parameters which produce thermal effects in the layers of skin below the stratum corneum, it is possible to retain a physically intact stratum corneum or to maintain a substantially unablated stratum corneum. It has been found that these treatment parameters can be used to create vacuoles under the stratum corneum while leaving the stratum corneum layer of the skin physically intact and producing few side effects in the region of skin that has been treated.

Many types of electromagnetic radiation can be used in the embodiments of this invention, including visible and infrared radiation and radar and radio waves. Coherent electromagnetic radiation, such as laser radiation, as well as non-coherent radiation, such as flashlamp radiation, can be used.

The lasers for use in the practice of the methods described herein include gas lasers, dye lasers, and solid-state lasers. Thus, the laser can be an argon ion gas laser, a carbon dioxide ($CO_2$) gas laser, a dye laser, a neodymim yttrium aluminum garnet (Nd:YAG) laser, an erbium YAG (Er:YAG) laser, an alexandrite laser, an erbium doped glass or fiber laser, a ytterbium doped glass or fiber laser, a thulium doped glass or fiber laser, or combinations thereof such as for example an erbium-ytterbium codoped fiber laser.

The electromagnetic wavelength can be selected such that it interacts with water as the primary or substantially only chromophore thereby limiting the damage of the stratum corneum, as the stratum corneum typically includes relatively small amounts of water (typically 10-20%), while the epidermis and dermis contain greater amounts of water (typically about 70%). Thus, the electromagnetic radiation wavelength can be selected to be between about 1200 nm to about 2000 nm, preferably between 1400 nm to about 1800 nm, more preferably about 1500 nm to about 1600 nm, or any wavelength in between. Thus, the electromagnetic radiation wavelength can be 1510 nm, 1515 nm, 1520 nm, 1525 nm, 1530 nm, 1535 nm, 1540 nm, 1545 nm, 1550 nm, 1555 nm, 1560 nm, 1565 nm, 1570 nm, 1575 nm, 1580 nm, 1585 nm, 1590 nm, 1595 nm, and the like. Other wavelengths can be chosen to target other chromophores, such as elastin, collagen, sebum, hemoglobin, melanin, keratin, or other molecules present in the tissue.

Treatments of this invention can be conducted using a contact window placed against the tissue during treatment. For example, sapphire or diamond windows may be used for their high thermal conductivity and transparency to pertinent wavelengths of electromagnetic radiation. However, contact windows are not required for all embodiments of the present invention. Non-contact windows may be used, such as, for example, windows set at a constant height above the tissue surface.

A wide variety of discrete treatment zones of varying depths and shapes can be created using the treatment parameters described herein. The shape of the discrete treatment zone can be controlled using appropriate combinations of the laser parameters.

The shape of the discrete treatment zones can be affected by a combination of the wavelength of the electromagnetic radiation, the size and shape of the radiation beam, the focusing of the radiation, the flatness of the skin surface, and the radiation pulse parameters (e.g., energy, duration, frequency, etc.).

The wavelength, size, and shape of the radiation beam and the focusing of the radiation determines gross propagation properties of the beam inside the tissue. Size (e.g., diameter for a circular beam shape or cross-sectional width for a polygonal or irregularly shaped beam) and shape of the radiation beam, particularly as the radiation beam enters the tissue, typically affects the shape of the resulting discrete treatment zone. For example, a polygonal cross-section for the radiation beam may produce a polygonal columnar treatment zone, and a circular radiation beam cross-section typically produces a circular or oval treatment zone cross-section.

Focusing, or numerical aperture (N.A.), can be used for determining the ratio of the surface temperature of the tissue to the peak temperature reached in the most intensely affected zone. Embodiments of the present invention may include varying or alternating focal depths for one or more radiation beams impacting a given treatment zone. For example, such embodiments may include multiple radiation beams focused to different depths, or they may include a single beam that is focused to varying depths within a treatment zone. The magnitude of the temperature profile is determined in part by the radiation pulse energy.

Thus, in one aspect of the invention, the nonablative fractional electromagnetic irradiation of skin creates treatment zones with treatment zone widths of between about 10 µm to about 500 µm, about 30 µm to about 300 µm, or about 50 µm to about 120 µm. The treatment zones can have a fill factor of between about 1% and about 90% of the total treatment surface area, about 10% to about 50% of the total treatment surface area, or about 15% to about 25% of the total treatment surface area, or any surface area coverage in between.

In another aspect of the invention, nonablative fractional treatments of skin with electromagnetic radiation, where the treatment zones have minimum cross sectional diameters of between about 30 µm to about 500 µm, and where the treatment zones have a density of between about 15% to about 20% of the total treatment surface area the volumes of discrete vacuoles can be between about 0.01 nl and about 60 nl in the dermal and/or epidermal layer of the skin, or 0.05 nl to about 4 nl, or about 0.1 to about 1 nl. The electromagnetic radiation can be in the form of laser radiation.

In one aspect of the invention, the nonablative fractional electromagnetic irradiation of skin is emitted from a laser and creates a local fluence of about 10 J/cm$^2$ to about 3000 J/cm$^2$, preferably about 20 J/cm$^2$ to about 1000 J/cm$^2$, or more preferably about 100 J/cm$^2$ to about 1000 J/cm$^2$, or any value in between. Thus, for example, the fluence can be 150 J/cm$^2$, 200 J/cm$^2$, 250 J/cm$^2$, 300 J/cm$^2$, 400 J/cm$^2$, 600 J/cm$^2$, 800 J/cm$^2$, and the like. The local fluence can be chosen based on the wavelength and absorption of light, the focusing of the beam, and whether a contact plate or external cooling is used. The proper fluence can be determined experimentally by cross sectioning the skin and taking biopsies or by evaluating the clinical response of the skin following treatment.

A typical treatment with the Fraxel® SR laser system produces a pattern of microscopic thermal wounds that extended from approximately 200-900 µm into the dermis. This depth of thermal lesion depends not only on the pulse energy, but also on the size of the microbeam incident on the skin surface being treated. A fractional 1550 nm laser system with a 140 µm incidence spot size can produce irradiance levels that can create deep lesions without causing any discernible superficial disruption or ablation. A fractional 1550 nm laser system with a 60 µm spot size, on the other hand, can produce a much higher irradiance (>5× that of the 140 µm incidence spot size). As a result, the bulk of its laser energy can be photoacoustically coupled to disrupt the stratum corneum and the epidermis, producing larger vacuoles and shallower thermal lesions (or collagen coagulation/denaturation zones). Thus, vacuoles can be produced under the stratum corneum that have a depth of about 30 µm to about 1000 µm, preferably a depth of about 50 µm to about 500 µm, or more preferably a depth of about 100 µm to about 400 µm. Depth of the vacuole can be measured from the skin surface to the bottom of the vacuole. In one aspect of the invention, the vacuoles have a depth of at least about 200 µm, preferably at least about 250 µm, or more preferably at least about 300 µm. The vacuoles can further be characterized in having a width of about 10 µm to about 500 µm, preferably about 30 µm to about 300 µm, or more preferably about 50 µm to about 200 µm, or any value in between.

The methods and apparatus of the invention thus provide for the biological elimination process that is capable of removing coagulated dermal tissue, necrotic debris or other depositional material. Without being bound to a theory, this transport system depends on the presence of a weakened DE junction induced by the fractional photothermolysis treatment. Since a fractional laser system only treats a portion of the overall skin surface area, rapid healing can be achieved and coagulated epidermal tissue can quickly be exfoliated through the stratum corneum. Thus, the stratum corneum serves a dual role, maintaining barrier function to prevent problems such as microbial contamination and infection as well as permitting exfoliation of treated tissue. Unlike most laser resurfacing procedures, wherein epidermal and dermal components are removed immediately by laser ablation, the mechanism by which fractional photothermolysis removed dermal material takes advantage of normal physiological functions of the epidermis, mainly exfoliation that includes epidermal and papillary dermal components. The methods and apparatus of the invention have the advantage of minimizing the adverse clinical side effects associated with ablative skin resurfacing, and avoiding the questionable clinical efficacies of laser treatment often seen in nonablative dermal remodeling procedures.

Fractional photothermolysis can be used to produce a plurality of vacuoles within the layers of skin below the stratum corneum layer of the skin, particularly in the layers of the epidermis below the stratum corneum: the stratum lucidum, stratum granulosum, stratum spinosum, and stratum basale; the dermis, including the papillary layer of the dermis and the reticular layer of the dermis; the hypodermis or superficial fascia; and the layer of adipose tissue below the dermis. The depth and volume of the vacuoles can be determined by selecting the treatment conditions used to produce them, such as, for example, the wavelength of irradiation, the pulse energy, the size of the treatment zone, the density of the treatment zones, and the like.

Furthermore, the nonablative fractional electromagnetic irradiation that produce vacuoles in the layers of skin below the stratum corneum layer can be used for the transepidermal elimination of dermal and/or subcutaneous content. The vacuole or plurality of discrete vacuoles within the layers of skin below the stratum corneum can trap dermal content and transport the trapped dermal content for elimination through the stratum corneum. Thus, electromagnetic radiation, particularly fractional photothermolysis, can be used to produce vacuoles in the skin for the treatment of recalcitrant melasma, Hori's macule, tattoos, scars, post-inflammatory hyperpigmentation, pigmentary disorders, photoaging, and dermal depositional disorders such as mucinosis and amyloidosis.

For example, tattoos can be removed or lightened using the present invention. The tattooed area can be subjected to fractional photothermolysis to create vacuoles under the stratum corneum. The vacuoles can trap the pigment used for the creation of the tattoo. The trapped pigment can be transported through the skin for exfoliation through the stratum corneum without scarring of the epidermis. Following skin irradiation, a topical antibiotic ointment can be applied to the treated site and the skin area protected using a non-adherent dressing. Topical antibiotic ointments include Bacitracin, Neosporin, Polysporin, and Sulphadene. Alternatively, a topical cream such as Vitamin E cream may be used in place of the antibiotic ointment.

The tattooed area can be treated once or a plurality of time. For example, the patient can be scheduled to return anytime between one day and ten weeks afterward the treatment for subsequent evaluation of color change (i.e., lightening of the tattoo with minimal change in normal skin color) and alteration in skin texture. If the tattoo is still visible at the irradiated site, the same area can be irradiated again, as well as other areas of the skin. The treatment parameters can be changed depending on the results from the prior treatment. For example, a higher local fluence (increased preferably by 5-10%) can be used if the area treated was unresponsive to the prior FP treatment. Thus, repeated irradiations over multiple visits can be completed until a satisfactory lightening or elimination of the tattoo is established.

The methods and apparatus described herein can be equally applicable to the treatment of port wine stains and pigmented blemishes. For example, the methods and apparatus of the invention can be used for the transepidermal elimination of melanomas and other pigmented lesions. Melanomas are usually darker than surrounding healthy tissue. The dark color associated with melanomas is caused by increased production of melanin by tumor cells. Melanin is a strong absorber of ultraviolet (UV) and visible light, and normally protects cells from the deleterious effects of solar UV radiation. The area of the skin affected with melanin can be treated as described above for tattoos. For example, the skin area discolored by melanin can be subjected to fractional photothermolysis to create vacuoles under the stratum corneum. The vacuoles can trap the melanin and the trapped melanin can be transported through the skin for exfoliation through the stratum corneum without scarring of the epidermis. The area of the skin can be treated once or a plurality of time until the melanin is substantially eliminated.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1

Two healthy subjects of Fitzpatrick skin type II were treated on the abdomen with the 1550 nm fractional laser system (Reliant Technologies Inc., Palo Alto, Calif.) one day prior to abdominoplasty. An institutional review board approved the study protocol and informed consent was obtained from both subjects prior to participation in the study. Hair within the test sites was removed by shaving and topical anesthesia was locally administered an hour prior to laser treatment. Each laser treatment covered approximately 12 $cm^2$.

A plurality of treatment beams was delivered wherein each treatment beam was substantially single-mode, approximately Gaussian in shape, and was either 60 μm or 140 μm in diameter at the skin surface as measured to the $1/e^2$ intensity point. The first subject received treatment from the smaller diameter microbeams, and the second subject received treatment from the larger diameter microbeams, both at various pulse energy levels. Pulse energies ranged from 6-20 mJ, at four to sixteen passes to produce final spot densities of 1000-2000 microscopic zones (MTZs) per $cm^2$. In general, the higher the pulse energy, the lower the final spot density. Excision of the treated abdominal skin was performed during the abdominoplasty at 1 day post-laser treatment.

Following surgical excision, the subcutaneous fat was removed and the samples were cut into smaller pieces for processing by either frozen or paraffin sectioning. For frozen sectioning, the samples were embedded in Optimal Cutting Temperature Compound (IMEB Inc., San Marcos, Calif.). For paraffin sectioning, samples were fixed in 10% v/v neutral buffered formalin (VWR International, West Chester, Pa.) overnight and embedded in paraffin blocks. The frozen samples were sectioned into 13 μm thick slices and stained with hematoxylin and eosin (H&E) and lactate dehydrogenase (LDH) while the paraffin embedded samples were sectioned into 10 μm thick slices and stained with H&E, Masson trichrome, and Fontana Masson. Elastin staining was performed according to the published protocol of G. Schwinder, K. Zanger and H. Greven ("Structural and mechanical aspects of the skin of Bufo marinus (Anura, Amphibia)," *Tissue & Cell* 33(5), 541-547 (2001)). Histological sections were imaged and recorded using a Leica® DM LM/P microscope and a DFC320 digital camera (Leica Microsystem, Cambridge, United Kingdom).

All laser exposures produced a constant pattern of well-spaced MTZs. FIG. 1A-D shows examples of histological sections obtained from abdominal skin processed with a variety of stains 1 day post-fractional photothermolysis. Using a laser pulse energy of 20 mJ, 60 μm incidence microbeam spot size, and spot density of 2000 $MTZ/cm^2$, a clearly demarcated dermal lesion representing collagen coagulation or denaturation was detected by H&E (FIG. 1A). Dermal collagen was stained blue by Masson trichrome (FIG. 1B). An epidermal vacuole overlying the thermal lesion was evident (FIGS. 1A and 1B). LDH staining indicated that the vacuolar content lacked viability (nonviable zone is not stained by Nitro Blue Tetrazolium Chloride; FIG. 1C). To test for the presence of melanin in the vacuole, the samples were stained with Fontana Masson. FIG. 1D demonstrates darkly stained granules within the vacuole, consistent with melanin. Thus, each vacuole contained both epidermal and dermal material.

Figure 2:
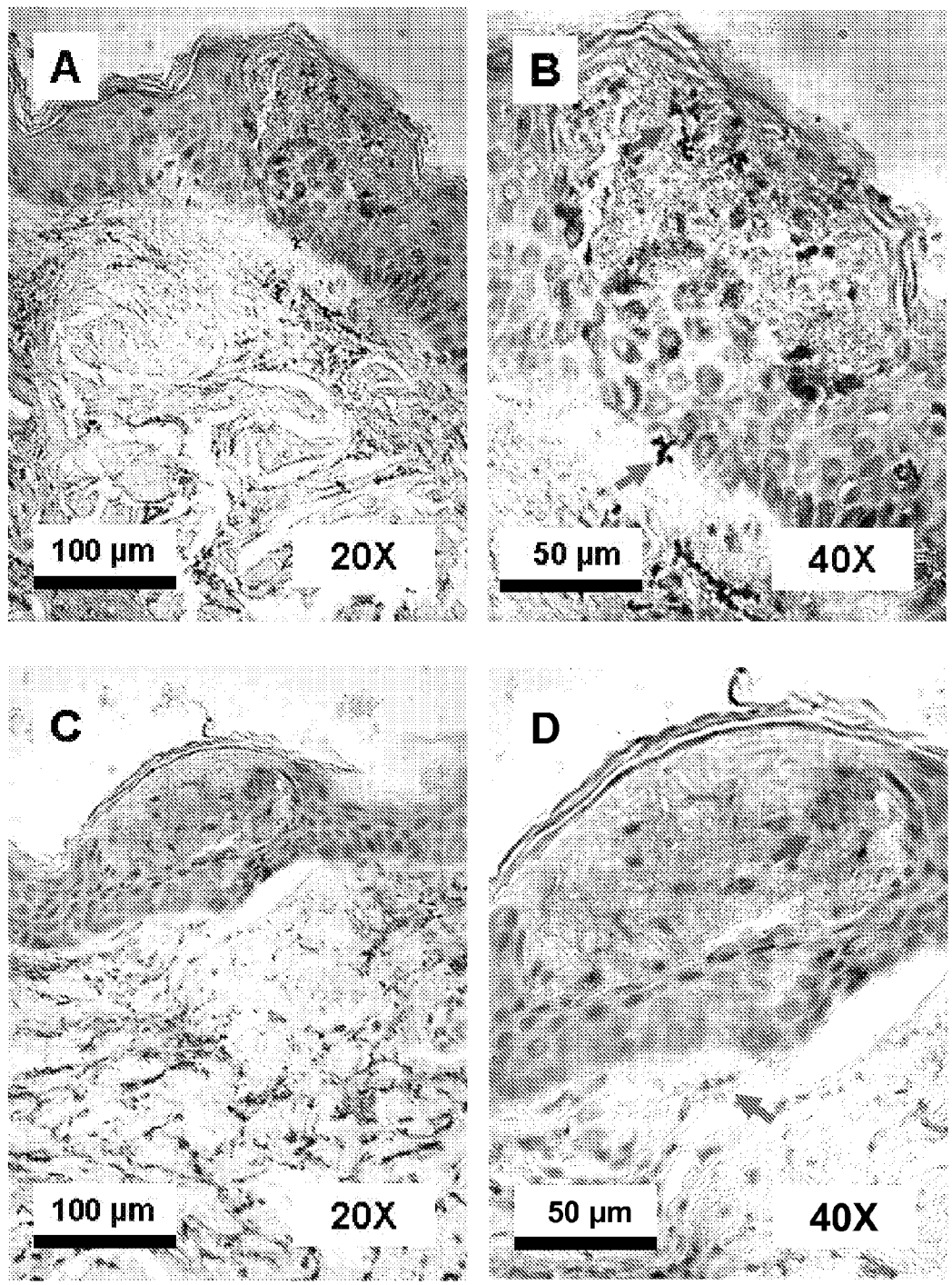
FIG. 2 illustrates the paraffin embedded tissue specimen stained using mouse anti-human elastin antibody 1 day after fractional photothermolysis.

The tissue sections were immunohistochemically stained for the detection of elastin within the laser-induced epidermal vacuole. FIG. 2 demonstrates tissue specimens stained with mouse anti-human elastin antibody at 1 day post-treatment at a pulse energy of 20 mJ and spot size of 140 μm. The tissue sections developed with 3,3'-Diaminobenzidine (DAB) showed the presence of elastin just beneath the DE junction in the dermis (FIG. 2A) as well as in the media layer of deeper medium-sized arterioles. The elastin was absent throughout the epidermis, except within vacuoles as clearly depicted at a higher magnification (FIG. 2B). To ensure that the material stained was not melanin, the tissue sections were processed with Vector® Novared (FIG. 2C), which stained the elastin fibrils a bright orange to a dark red color. FIG. 2D shows a higher magnification image of another vacuole stained with Novared with an identical morphology to material located just beneath the DE junction. Thus, dermal material was present with the epidermal vacuole.

Figure 3:
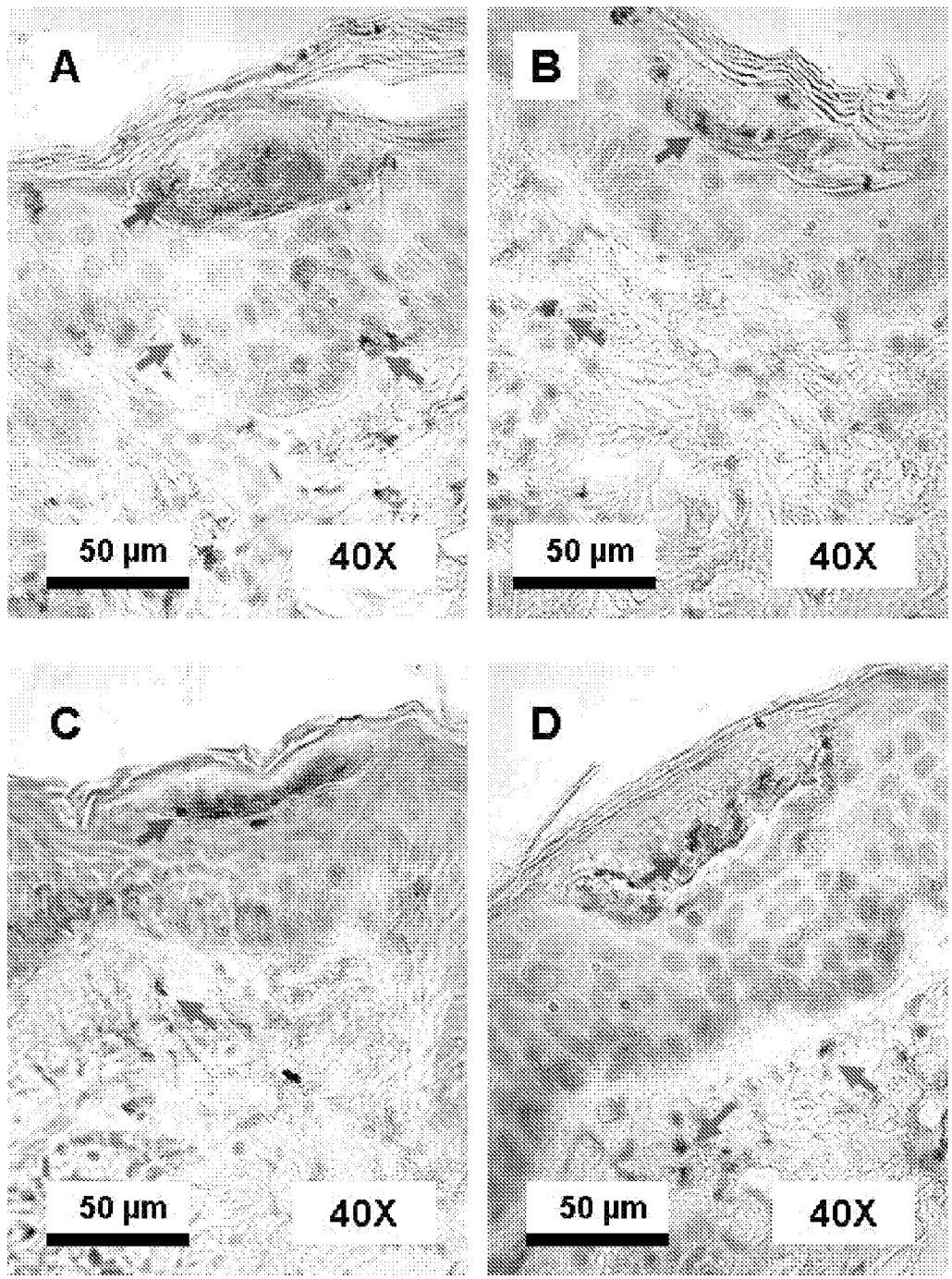
FIG. 3 illustrates the paraffin embedded histological sections obtained from abdominal skin 1 day after fractional photothermolysis.

Larger vacuoles were formed using the larger 1400 µm spot size treatment. However, the incidence spot size and the resulting vacuolar dimension did not appear to affect the transport of elastin through the DE junction. Both (60 µm and 140 µm) modes of treatment produced consistent transfer of elastin from the dermal compartment into the epidermal vacuole. Similar results were obtained when the pulse energy was reduced by up to 70%. Epidermal vacuoles stained positively for elastin at pulse energies of 6 mJ and 10 mJ for both 60 µm (FIGS. 3A and 3B) and 140 µm (FIGS. 3C and 3D) incidence spot sizes. Further testing revealed consistent transfer of elastin from the dermal compartment into epidermal vacuoles following fractional photothermolysis treatment at pulse energies spanning 6-20 mJ and spot sizes of either 60 µm or 140 µm.

The results thus show the laser-dependent transepidermal transport system capable of eliminating dermal material. The treatment of the skin with a laser operated at an incidence $1/e^2$ microbeam spot size of 60 µm or 140 µm with variable pulse energies and densities resulted in elastin being trapped in epidermal vacuoles created by treatment with fractional photothermolysis. The elastin in the vacuoles can migrate to the surface and be eliminated.

Example 2

Melanin, which is the pigment that colors the epidermis and/or the dermis, originates from melanocytes in the basal cell layer. If the basal layer is removed, a new basal layer must be regenerated in order to provide pigment to the overlying epidermis. To treat an area of skin with melanin, the hair in the treatment area is removed using conventional stripping methods, and, optionally, an antibiotic or a pain killer is massaged into the skin. A handpiece delivering 1550 nm laser light is used to directly irradiate the skin with a laser pulse energy of 20 mJ, 60 µm incidence microbeam spot size, and spot density of 3000 $MTZ/cm^2$. This irradiation creates a plurality of vacuoles within the layers of skin below the stratum corneum layer of the skin while leaving the stratum corneum substantially intact. The treatment results in necrosis and/or denaturation of some of the skin containing melanin without ablation of the stratum corneum. The skin sloughs off these treated cells naturally through exfoliation, which is accelerated by the treatment. By this means, removal of melanin is achieved.

The entire laser treatment is carried out in a period of minutes, depending upon the size of the treatment area. The level of melanin removal can be evaluated at a subsequent visit, and further treatments applied to achieve the desired level of removal of melanin from skin.

All printed patents and publications referred to in this application are hereby incorporated herein in their entirety by this reference.

While the preferred embodiment of the invention has been illustrated and described, it will be appreciated that various changes can be made therein without departing from the spirit and scope of the invention.

The invention claimed is:

1. A method for eliminating dermal content through the skin, the method comprising:
exposing a region of the skin to laser radiation to create a plurality of treatment zones, wherein the treatment leaves stratum corneum within each treatment zone substantially intact and creates a vacuole below the stratum corneum within each treatment zone; and
encompassing the dermal content in the vacuole of each treatment zone,
wherein the dermal content is exfoliated through the skin, the laser radiation has a wavelength between 1200 nm to 2000 nm, the laser radiation has a pulse energy of 1 mJ to 50 mJ per treatment zone, the laser radiation has a spot size of 10 µm to 400 µm, each vacuole has a depth of 50 µm to 1000 µm, and the treatment zones have a fill factor of between 1% and 90% of a total treatment surface area.

2. The method of claim 1, wherein the laser radiation has a wavelength between 1500 nm to 1600 nm.

3. The method of claim 1, wherein the laser radiation has a pulse energy of 5 mJ to 40 mJ per treatment zone.

4. The method of claim 3, wherein the laser radiation has a pulse energy of 6 mJ per treatment zone.

5. The method of claim 3, wherein the laser radiation has a pulse energy of 20 mJ per treatment zone.

6. The method of claim 1, wherein the laser radiation has a spot size of 40 µm to 200 µm.

7. The method of claim 1, wherein the laser radiation has a spot size of 20 µm to 120 µm.

8. The method of claim 1, wherein the laser radiation has a spot size of 60 µm.

9. The method of claim 1, wherein the laser radiation has a spot size of 140 µm.

10. The method of claim 1, wherein the treatment zone width is 10 µm to 500 µm.

11. The method of claim 10, wherein the treatment zone width is 30 µm to 500 µm.

12. The method of claim 1, wherein each vacuole is present in the dermal layer of the treated region of the skin.

13. The method of claim 1, wherein each vacuole is present below the dermal layer of the treated region of the skin.

14. The method of claim 1, wherein each vacuole has a depth of 100 µm to 500 µm.

15. The method of claim 1, wherein each vacuole has a volume of 0.01 nl to 60 nl.

16. The method of claim 1, wherein each vacuole has a volume of 0.05 nl to 4 nl.

17. The method of claim 1, wherein the dermal content comprises material from a region of tissue with a condition selected from the group consisting of recalcitrant melasma, Hori's macule, tattoo, post-inflammatory hyperpigmentation, solar elastosis, mucinosis, amyloidosis, and scar tissue.

18. The method of claim 17, wherein the dermal content comprises melanin.

19. The method of claim 17, wherein the dermal content comprises tattoo particles.

20. The method of claim 17, wherein the dermal content comprises scar tissue.

21. The method of claim 1, wherein the electromagnetic radiation treatment is a skin resurfacing treatment.

22. The method of claim 1, wherein the electromagnetic radiation treatment is a fractional photothermolysis treatment.

23. A method of eliminating tattoos, the method comprising:
exposing a region of the skin to laser radiation to create a plurality of treatment zones, wherein the treatment leaves stratum corneum within each treatment zone substantially intact and creates a vacuole below the stratum corneum within each treatment zone; and encompassing ink of the tattoos in each vacuole wherein the ink is exfoliated through the skin, the laser radiation has a wavelength between 1200 nm to 2000 nm, the laser radiation has a pulse energy of 1 mJ to 50 mJ per treatment zone, the laser radiation has a spot size of 10 µm to 400 µm, each vacuole has a depth of 50 µm to 1000 µm, and the treatment zones have a fill factor of between 1% and 90% of a total treatment surface area.

24. The method of claim 23, wherein the laser radiation has a wavelength between 1500 nm to 1600 nm.

25. The method of claim 23, wherein the laser radiation has a pulse energy of 5 mJ to 40 mJ per treatment zone.

26. The method of claim 25, wherein the laser radiation has a pulse energy of 6 mJ per treatment zone.

27. The method of claim 26, wherein the laser radiation has a pulse energy of 20 mJ per treatment zone.

28. The method of claim 23, wherein the laser radiation has a spot size of 40 µm to 200 µm.

29. The method of claim 23, wherein the laser radiation has a spot size of 20 µm to 120 µm.

30. The method of claim 23, wherein the laser radiation has a spot size of 60 µm.

31. The method of claim 23, wherein the laser radiation has a spot size of 140 µm.

32. The method of claim 23, wherein the treatment zone width is 10 µm to 500 µm.

33. The method of claim 32, wherein the treatment zone width is 30 µm to 500 µm.

34. The method of claim 23, wherein each vacuole is present in the dermal layer of the treated region of the skin.

35. The method of claim 23, wherein each vacuole is present below the dermal layer of the treated region of the skin.

36. The method of claim 23, wherein each vacuole has a depth of 100 µm to 500 µm.

37. The method of claim 23, wherein each vacuole has a volume of 0.01 nl to 60 nl.

38. The method of claim 23, wherein each vacuole has a volume of 0.05 nl to 4 nl.

39. The method of claim 23, wherein the electromagnetic radiation treatment is a fractional photothermolysis treatment.

* * * * *

UNITED STATES PATENT AND TRADEMARK OFFICE
CERTIFICATE OF CORRECTION

| | | |
|---|---|---|
| PATENT NO. | : 8,690,863 B2 | Page 1 of 1 |
| APPLICATION NO. | : 11/548248 | |
| DATED | : April 8, 2014 | |
| INVENTOR(S) | : Kin F. Chan et al. | |

It is certified that error appears in the above-identified patent and that said Letters Patent is hereby corrected as shown below:

In the Specification

At column 1, line number 30, after "granulosum" insert --,--

At column 2, line number 46, change "gasses" to --gases-- and at line number 67 change "produce" to --produces--

At column 3, line number 5, change "penetrate" to --penetrates-- and at line 7 change "produce" to --produces--

At column 5, line number 37, change "portion" to --portions--

At column 9, line number 20, change "time" to --times-- and at line number 22 change "afterward" to --after-- and at line 51 change "time" to --times--

At column 11, line number 13, change "_m" to --µ-- and at line 14 change "_m" to --µ-- and at line number 24 change "▢m" to --µ-- and at line number 25 change "▢m" to --µ--

Signed and Sealed this
Eighth Day of July, 2014

Michelle K. Lee
*Deputy Director of the United States Patent and Trademark Office*